United States Patent
Jeon et al.

(10) Patent No.: US 10,322,980 B2
(45) Date of Patent: Jun. 18, 2019

(54) METHOD OF UPGRADING LOW-VALUE LINEAR ALPHA-OLEFINS OF C18 OR MORE

(71) Applicants: SK INNOVATION CO., LTD., Seoul (KR); SK LUBRICANTS CO., LTD., Seoul (KR)

(72) Inventors: Hee Jung Jeon, Daejeon (KR); Jin Hee Ok, Busan (KR); Tae Jin Kim, Seoul (KR); Wan Seop Kwon, Daejeon (KR)

(73) Assignees: SK Innovation Co., Ltd., Seoul (KR); SK Lubricants Co., Ltd., Seoul (KR)

( * ) Notice: Subject to any disclaimer, the term of this patent is extended or adjusted under 35 U.S.C. 154(b) by 451 days.

(21) Appl. No.: 14/693,326

(22) Filed: Apr. 22, 2015

(65) Prior Publication Data
US 2015/0322365 A1    Nov. 12, 2015

(30) Foreign Application Priority Data
Apr. 25, 2014    (KR) .................. 10-2014-0050078

(51) Int. Cl.
*C07C 5/03*    (2006.01)
*C10M 107/10*    (2006.01)

(52) U.S. Cl.
CPC ............ *C07C 5/03* (2013.01); *C10M 107/10* (2013.01); *C10M 2205/0285* (2013.01); *C10M 2205/173* (2013.01); *C10N 2220/022* (2013.01); *C10N 2220/023* (2013.01); *C10N 2260/02* (2013.01); *C10N 2270/00* (2013.01)

(58) Field of Classification Search
USPC .................. 585/310–332, 500–671
See application file for complete search history.

(56) References Cited

U.S. PATENT DOCUMENTS

| | | | | |
|---|---|---|---|---|
| 5,120,891 A | * | 6/1992 | Sanderson | B01J 29/08 585/255 |
| 6,281,404 B1 | * | 8/2001 | Miller | C07C 5/2518 585/666 |
| 2004/0181111 A1 | | 9/2004 | Sigl et al. | |
| 2007/0131579 A1 | | 6/2007 | Koivusalmi et al. | |
| 2008/0171675 A1 | * | 7/2008 | Yeh | C10M 101/02 508/110 |

FOREIGN PATENT DOCUMENTS

| | | |
|---|---|---|
| CA | 1167477 A1 | 5/1984 |
| CN | 1981932 A | 6/2007 |
| CN | 101200666 A | 6/2008 |

(Continued)

OTHER PUBLICATIONS

Sasol, PURAL/CATAPAL fact sheet.*
(Continued)

*Primary Examiner* — In Suk C Bullock
*Assistant Examiner* — Ali Z Fadhel
(74) *Attorney, Agent, or Firm* — Abelman, Frayne & Schwab (57) ABSTRACT

Disclosed is a method of manufacturing high-quality lube base oil, by converting a low-value linear alpha-olefin having a C18 or more hydrocarbon chain into a linear internal-olefin having a controlled double bond position distribution and then oligomerizing the linear internal-olefin.

20 Claims, 4 Drawing Sheets

(56) References Cited

FOREIGN PATENT DOCUMENTS

| EP | 0136377 B2 | 1/1992 |
| EP | 1466881 A2 | 10/2004 |
| EP | 1719747 A1 | 11/2006 |
| JP | 5-306241 | 11/1993 |

OTHER PUBLICATIONS

Lutz, "Zeolite Y: Synthesis, Modification, and Properties—A Case Revisited, Advances in Materials Science and Engineering, vol. 2014, Article ID 724248, 20 pages, Published May 22, 2014".*
Ramser and Hill, "Physical Structure of Silica-Alumina Catalysts", Industrial and Engineering Chemistry, vol. 50, No. 1, Jan. 1958, p. 117-124.*
Zeynali, "Effect of catalyst pore size on styrene production rate", diffusion-fundamentals.org, 13 (2010) 2, pp. 1-18. (Year: 2010).*
European Search Report for EP 15 16 4804 dated Sep. 16, 2015 (6 pages).
Chinese Office Action dated Sep. 28, 2017 for CN 201510204824.5.

* cited by examiner

METHOD OF UPGRADING LOW-VALUE LINEAR ALPHA-OLEFINS OF C18 OR MORE

CROSS-REFERENCE TO RELATED APPLICATION

This application claims the benefit of Korean Patent Application No. 10-2014-0050078, filed Apr. 25, 2014, entitled "Method for upgrading low-valued linear alpha-olefins of C18 or more", which is hereby incorporated by reference in its entirety into this application.

BACKGROUND OF THE INVENTION

1. Technical Field

The present invention relates to a method of upgrading low-value linear alpha olefins (LAOS) of C18 or more. More particularly, the present invention relates to a method of manufacturing high-quality lube base oil by converting a low-value LAO having a C18 or more hydrocarbon chain into a linear internal-olefin (LIO) having a controlled double bond position distribution, which then undergoes oligomerization.

2. Description of the Related Art

Ethylene is a raw material used in the chemical industry to the extent that the production and consumption thereof are considered as indicators of the chemical industry scale of a country. Typically, ethylene is employed as a monomer for preparing a polymer such as polyethylene. In some cases, LAOs having a C4-C40 carbon length (or chain) are prepared by adjusting the degree of polymerization of ethylene, and thus utilized to manufacture a variety of chemicals. In this regard, as used herein, the term "full range LAO" refers to a C4-C40 LAO mixture resulting from ethylene polymerization or oligomerization.

The reason why LAO production techniques are important is that LAO is a chemical without sulfur and nitrogen derived from crude oil. Generally, since crude oil contains impurities such as sulfur and nitrogen components in amounts of ones of wt %, it is difficult to directly prepare chemicals composed of pure hydrocarbons without such impurities. However, ethylene resulting from catalytic cracking of crude oil is converted into LAO, which is then converted again into a desired chemical, thereby obtaining chemicals composed of pure hydrocarbons without impurities.

Ethylene polymerization is mainly carried out using a batch reactor under air-sensitive conditions in the presence of a metallocene catalyst. Since a metallocene catalyst has a very strong single acid site, ethylene is selectively polymerized at the single acid site of the catalyst, and is thus linearly grown at the acid site of the catalyst. Ultimately, the olefin produced by the LAO preparation reaction possesses a linear alpha-olefin structure having an even number of carbon atoms because of the use of an ethylene monomer.

When operating conditions for the LAO preparation reaction are controlled, the LAO composition distribution may be altered. For example, when the reaction temperature or the polymerization time is increased, the proportion of LAO having a relatively high molecular weight may become high. In contrast, when the reaction temperature or the polymerization time is decreased, the proportion of LAO having a relatively low molecular weight may increase. Taking into consideration the industry scale for LAO-derived chemicals by LAO manufacturers, the LAO composition is changed in such a manner that the reaction conditions are appropriately controlled, thereby ensuring optimal profitability for individual projects.

Alpha-olefins produced by the LAO preparation processes exhibit properties varying depending on the number of carbon atoms thereof, and the properties of the resulting chemicals may become different depending on the type of LAO feed. For example, C4 LAOs obtained by polymerizing two ethylene monomers are present in a gas phase, and polymers resulting from the polymerization thereof have an excess of intramolecular branches, making it difficult to apply to a specific product, for example, lube base oil. Also, even when C6 LAOs obtained by polymerizing three ethylene monomers are converted into polymers, such polymers are unlikely to be applied to lube base oil and so on due to many intramolecular branches thereof. As such, copolymerization of ethylene with a C6 LAO may result in an ethylene-1-hexene copolymer having properties different from those of conventional polyethylene. Also, C8 LAOs obtained by polymerizing four ethylene monomers may be applied to Group IV lube base oil via polymerization, and may be used to produce a copolymer with ethylene, as in the C6 LAOs. Also, C10-C12 LAOs are polymerized and thus mainly used as Group IV base oil, and C14-C16 LAOs are reacted with amine or succinic acid, so that the resulting products may be applied to various functional chemicals, or mixed and thus used for cheap drilling oil.

The aforementioned LAOs have certain end-uses, and the markets adapted for the demand thereof are established. Furthermore, the related techniques have been already developed to some extent. The most expensive LAO is a C8-C12 LAO for preparing high-quality lube base oil (e.g. Group IV lube base oil), and C6 and C8 LAOs may be mainly utilized because the demand thereof is high for producing copolymers. Also, although C14-C16 LAOs are relatively less used due to limited end-uses thereof compared to the C6-C12 LAOS, C14-C16 LAOs may be used to prepare specialty chemicals and may thus be formed into products by increasing purity thereof. However, C18 or more LAOs are problematic because the end-uses thereof are limited, and the purity thereof has to be increased to obtain desired products. In this regard, C18 or more LAOs have been employed as an additive for lube oil or in wax form, but are not general-purpose chemical products, and thus the demand thereof is undesirably low. Also, C20 or more LAOs are limited in serving as feeds because they exist as a solid at room temperature. Like this, the market prices of C18 or more LAOs are maintained very low compared to the other LAOS, on account of low demands, tendencies to exist as a solid, and restrictions where such feeds may be prepared into products only when the purity thereof is increased.

Owing to the limitations of end-uses as above, the yield of high-value C8-C12 LAOs is intended to be selectively increased while decreasing the yield of C18 or more LAOs, by LAO manufacturers. However, the LAO products have a composition of the normal distribution due to characteristics of the polymerization catalyst, making it impossible to attain operating conditions for preparing only C8-C12 LAOs and for drastically lowering the yield of C18 or more LAOS.

Hence, LAO preparation under reaction conditions able to lower the yield of C18 or more LAOs as much possible is chosen by LAO manufacturers, and is advantageous because only LAOS, the demand of which is high and the value of which is also high, may be selectively prepared while decreasing the yield of C18 or more LAOs regarded as byproducts. However, since the composition of products resulting from ethylene polymerization has the normal distribution as mentioned above, the yield of C8-C12 LAOS, corresponding to feeds for end-uses (especially Group IV lube base oil) which have the highest price and a future market of which is expected to grow, is relatively low, which is undesirable.

Alternatively, the reaction conditions may be set so as to maximize the yield of the most expensive C8-C12 LAOs without taking into account the yield of C18 or more LAOS. As such, the yield of C18 or more LAOs is 10 wt % or more, but the yield of relatively high-value C8-C12 LAOs may be increased. Therefore, if C18 or more LAOs obtained by full range LAO techniques can be simply converted into general-purpose high-value products, the effect of such technology is expected to be very significant. Accordingly, methods of converting C18 or more LAOs into high-value chemicals are required.

Meanwhile, techniques for preparing chemicals (e.g. drilling oil) having improved properties in such a manner that a double bond present at the alpha position of the LAO is shifted to the inside of the carbon chain to form a linear internal-olefin (LIO) (olefin shift reaction) are also known (e.g. U.S. Pat. No. 6,281,404). However, the above techniques are not regarded as the application of low-value C18 or more LAOs because a wide range of C4-C50 LAOs are utilized, and also because the double bond shift reaction for 1-pentene is mainly disclosed. In addition, there are known techniques for manufacturing lube base oil (e.g. EP 0 136 377 B1) by oligomerizing internal olefins (especially, internal olefin produced from dehydrogenation of paraffin so that a double bond is randomly distributed in the molecule) in the presence of a boron trifluoride catalyst and a promoter, and for manufacturing lube base oil (Japanese Patent Application Publication NO. 1993-306241) by oligomerizing a C10-C24 LAO/LIO mixture. However, these techniques are limited in improving properties of the lube base oil because the position of the double bond in the olefin is not controlled. In particular, such techniques are unlikely to become technology for increasing the value of low-value C18 or more LAOS produced inevitably as byproducts in full range LAO preparation.

SUMMARY OF THE INVENTION

Therefore, an embodiment of the present invention is intended to provide a method of manufacturing high-quality lube base oil (e.g. Group III or Group III+ lube base oil) from a low-value C18 or more LAO (especially, a C18 or more LAO derived from a full range LAO).

According to an embodiment of the present invention, there is provided a method of manufacturing lube base oil from a C18 or more LAO, comprising: a) providing a C18 or more LAO or a mixture thereof; b) converting the C18 or more LAO or mixture thereof into a C18 or more LIO or a mixture thereof by a double bond shift reaction at a temperature ranging from 250° C. to less than 400° C. in the presence of a catalyst having a weak acid site; and c) oligomerizing the C18 or more LIO or mixture thereof, thus synthesizing a hydrocarbon in a lube base oil range, wherein in b), a weight reduction of the C18 or more LIO or mixture thereof relative to the C18 or more LAO or mixture thereof is 5% or less, in c), the hydrocarbon in the lube base oil range has a $\alpha/\beta$ value of 1~10 (where a is the number of carbon atoms of the longest carbon chain in the hydrocarbon, and $\beta$ is the number of carbon atoms of the shortest carbon chain in the hydrocarbon), and includes a dimer (D) and a trimer or more (T+) hydrocarbon of the C18 or more LIO or mixture thereof, with a D/T+ weight ratio ranging from 0.1 to 100, and the lube base oil has a viscosity index of at least 130, a pour point of −20° C. or less, and a cloud point of −20° C. or less.

In an exemplary embodiment, the C18 or more LAO provided in a) may be a C18 or more LAO having an even number of carbon atoms, derived (separated) from a C4-C40 full range LAO produced by ethylene polymerization or oligomerization.

In an exemplary embodiment, the number of carbon atoms of the longest carbon chain in a molecular structure of the hydrocarbon in the lube base oil range may approximately fall in the range of 18~60.

In an exemplary embodiment, b) may be performed at a temperature of about 300~375° C.

In an exemplary embodiment, b) may be performed at a pressure of about 4~10 bar.

In an exemplary embodiment, b) may be performed in a fixed bed reactor at a weight hourly space velocity (WHSV) of about 0.01~50 hr$^{-1}$ at an inactive carrier gas flow rate of about 10~1000 sccm.

In an exemplary embodiment, the C18 or more LAO provided in a) may further comprise a C18 or more LAO derived from Fischer-Tropsch reaction. As such, the C18 or more LAO derived from Fischer-Tropsch reaction may be contained in an amount of about 50 wt % or less.

In an exemplary embodiment, the method may further comprise performing isomerization to additionally improve low-temperature properties, before and/or after c).

In an exemplary embodiment, the method may further comprise performing hydrogenation to remove a double bond from a hydrocarbon molecule, after c).

According to embodiments of the present invention, a low-value C18 or more LAO (especially, a C18 or more LAO derived from a full range LAO resulting from ethylene polymerization or oligomerization) can be converted into a C18 or more LIO while controlling the position shift of a double bond therein, after which such a C18 or more LIO is oligomerized, thereby manufacturing lube base oil satisfying requirements of Group III or more. In particular, since a reduction in the number of carbon atoms can be maximally suppressed during the conversion into LIO (i.e. a weight reduction can be suppressed), it is possible to manufacture lube base oil having uniform properties. Also, the lube base oil manufactured according to the present embodiment has an X-shaped hydrocarbon structure, and thus the pour point and the cloud point thereof can be effectively lowered, advantageously obviating an isomerization reaction that is essentially performed in conventional processes for manufacturing high-quality lube base oil. Also, a C18 or more LAO, the value of which is the lowest among olefin components of a conventional full range LAO, can be converted into the LIO via simple reaction, without the need to increase the purity thereof through a distillation process that requires the high device and operation costs, thus facilitating commercialization thereof to thereby expect wide applications in future.

DESCRIPTION OF SPECIFIC EMBODIMENTS

Hereinafter, a detailed description will be given of specific embodiments of the present invention, which are not construed as limiting the present invention.

According to an embodiment of the present invention, a C18 or more LAO (or mixtures thereof) is converted into the corresponding C18 or more LIO (or mixtures thereof) by an olefin shift (double bond shift) reaction, after which the C18 or more LIO is oligomerized, thus obtaining lube base oil.

As used herein, "lube base oil" refers to a hydrocarbon typically having a boiling point of about 300° C. or more (particularly about 340~700° C.) and a viscosity of about 2 cSt or more at 100° C.

Reaction for Producing Lube Base Oil from C18 or More LAO

Linear olefins having the same molecular weight may have different three-dimensional structures and properties depending on the position of double bond in the olefin. Thus, the structures and properties of olefin oligomers obtained by olefin polymerization may vary depending on the structure of the olefin feed.

As for factors affecting the properties of the products obtained by olefin oligomerization, for example, when an olefin dimer is an X-shaped hydrocarbon, the longest carbon chain length (the number of carbon atoms) and the shortest carbon chain length (the number of carbon atoms) in the molecular structure are taken into consideration. Specifically, when the longest and the shortest carbon chain length are referred to as $\alpha$ and $\beta$, respectively, the viscosity index is increased with an increase in $\alpha/\beta$, and also a pour point and viscosity are increased. On the other hand, as the $\alpha/\beta$ value is lower, a pour point is decreased, and the viscosity index is comparatively reduced. As such, the $\alpha/\beta$ value may be determined through correlation between the results of NMR analysis and Simdist analysis.

In this regard, lube base oil has superior properties with an increase in viscosity index and a decrease in pour point. Actually, since the pour point and the viscosity index vary in the same direction depending on changes in the hydrocarbon structure, the molecular structure of the hydrocarbon has to be appropriately controlled in order to attain optimal properties.

Figure 1:
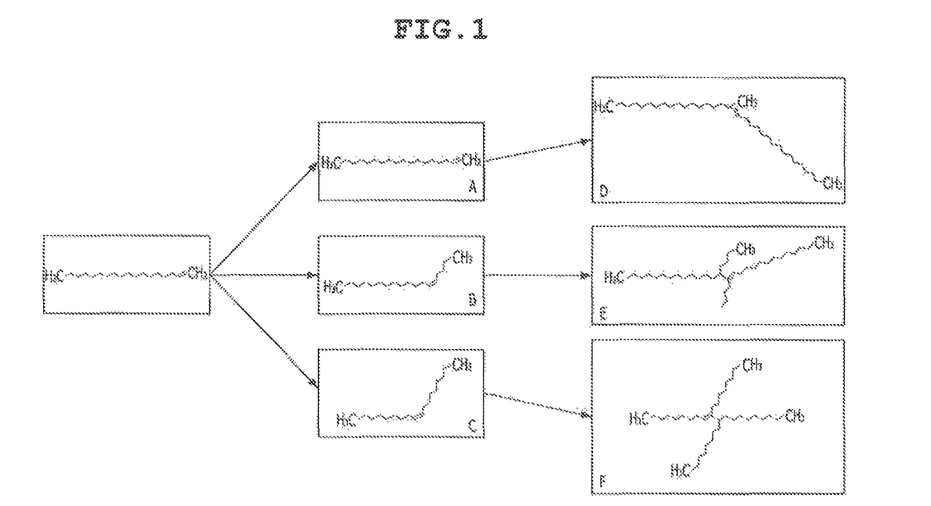
FIG. 1 schematically illustrates a reaction route (D) for direct oligomerization of a C18 or more LAO into a dimer, and reaction routes (E and F) for oligomerization of C18 or more LIOs obtained by different olefin shifts to prepare dimers.

FIG. 1 schematically illustrates a reaction route (D) for direct oligomerization of a C18 or more LAO into a dimer, and reaction routes (E and F) for oligomerization of C18 or more LIOs obtained by different olefin shifts to prepare dimers.

As illustrated in FIG. 1, even when using the linear olefins (A, B, and C) having the same molecular weight, chemical structures of dimers produced by oligomerization may become different depending on the position of double bond in the olefin. Specifically, the oligomerization of a C18 LAO having a double bond at an alpha-position results in a dimer (D) having linear properties. As such, the molecule of the dimer (D) is configured such that the longest carbon chain is C35 and the shortest carbon chain is C2, and thus the $\alpha/\beta$ value equals 17.5.

On the other hand, when a C18 LIO (13) in which a double bond is shifted to Position 5 in the carbon chain is oligomerized, a dimer (E) is produced. The molecule of the dimer (E) is configured such that the longest carbon chain is C28 and the shortest carbon chain is C10, and thus the $\alpha/\beta$ value is 2.8.

Also, when a C18 LIO (center linear internal olefin; center olefin) in which a double bond is positioned at the center of the carbon chain is oligomerized, a dimer (F) is produced. The structure of the dimer (F) is configured to include the longest carbon chain of C20 and the shortest carbon chain of C18, and thus the $\alpha/\beta$ value is 1.1.

In this regard, as the $\alpha\beta$ value is lower, namely, is D→E→F, the viscosity index and the pour point may decrease. Therefore, to satisfy the requirements of high-quality lube base oil in terms of viscosity index and pour point, the $\alpha/\beta$ value of the oligomerization product needs to be maintained in a predetermined range. This means that a double bond shift reaction for converting a C18 or more LAO into the corresponding LIO should be appropriately controlled.

Table 1 below show the kinds of lube base oil depending on the properties specified in the API.

TABLE 1

|  | Viscosity Index | Sulfur (wt %) | Pour point (° C.) | Saturate (wt %) |
| --- | --- | --- | --- | --- |
| Group I | 80 to 119 | >0.03 | −5 to 15 | <90 |
| Group II | 80 to 119 | ≤0.03 | −10 to −20 | ≥90 |
| Group III | ≥120 | ≤0.03 | −10 to −25 | ≥90 |
| Group III+ | ≥140 | ≤0.03 | −15 to 30 | >90 |
| Group IV | 135 to 140 | — | −53 | — |
| Group V | 140 | — | −21 | — |

As is apparent from Table 1, the most important properties that determine the rating of lube base oil are viscosity index, sulfur content, pour point, and saturate content. When sulfur content is typically limited to 0.03 wt % or less, properties of lube base oil corresponding to Group III or more may be obtained. Also, saturated hydrocarbon-rich lube base oil having a viscosity index of 120 or more and a pour point of −10° C. or less (−20° C. or less in an actual lube base oil preparation process) may satisfy the requirements for the rating of Group III or more. In this regard, "viscosity index" refers to an indicator that shows a change in viscosity depending on the temperature. Also, "pour point" refers to a limit temperature that allows a liquid phase to flow. Typically, a pour point is increased in the presence of a linear long carbon chain (long linear type), and is decreased with an increase in the number of branched chains.

In Table 1, Group IV lube base oil is typically prepared from C8-C12 LAO, and is known as PAO (Poly Alpha Olefin). Group III lube base oil is generally derived from crude oil, and is produced by converting a heavy hydrocarbon of the crude oil into long-chain paraffin in the presence of hydrogen, followed by skeletal isomerization to reduce a pour point. Also, lube base oil having a viscosity index or a pour point, which are high compared to Group III base oil but are low compared to Group IV base oil, is known as Group III+ lube base oil.

As for lube base oil manufactured according to an embodiment, the oligomerization feed is LIO in which a double bond is mainly present in the middle portion of the carbon chain of the hydrocarbon, and the resulting oligomerization product has an X-shape, so that a pour point is very low, thus obviating the need for structural isomerization as additional hydrogenation treatment. In particular, the double bond shift reaction, which is carried out before oligomerization, is controlled, without a change in the feed and/or the use of an additive, and thereby properties of final lube base oil may be simply adjusted.

C18 or More LAO

According to an embodiment, a C18 or more LAO, for example, a C20 or more LAO, especially a C24-C36 LAO, may be used as a reaction feed. Particularly useful is a C18 or more LAO derived (separated) from a full range LAO prepared by ethylene polymerization (or oligomerization).

Generally, LAOs are produced by (i) cracking of paraffin, (ii) dehydrogenation of paraffin, (iii) dehydration of alcohol, (iv) Fischer-Tropsch reaction, and (v) oligomerization of ethylene. As such, LAOs produced by the reaction route (v) basically have an even number of carbon atoms. As used herein, a C4-C40 LAO produced by the reaction route (v) is defined as a full range LAO. The preparation process of such a full range LAO is known to be Chevron Phillips (or Gulf) processing, SHOP processing, MOS processing, and Ethyl processing.

Table 2 below shows the illustrative full range LAO compositions.

TABLE 2

| Number of carbon atoms | Amount (wt %) |
| --- | --- |
| C4-C8 | 50 |
| C10-C12 | 28 |
| C14-C16 | 17 |
| C18 or more | <5 |

In an exemplary embodiment, a C18 or more LAO derived from the full range LAO as above may be used alone as a reaction feed. In some cases, the feed may further include a C18 or more LAO derived from at least one of reaction routes (i) to (iv), or mixtures thereof.

More specifically, a C18 or more LAO derived from Fischer-Tropsch reaction may be additionally used. Selectively, a C18 or more LAO produced by decarboxylation/decarbonylation of biomass-derived fat containing triglyceride and/or fatty acid may be used together with the full range LAO. As such, examples of the biomass-derived fat may include animal fat (fish oil, beef tallow, lard, mutton tallow, butter, etc.), and vegetable oil (sunflower seed oil, canola oil, palm oil, corn oil, soybean oil, castor oil, cocoa butter, palm kernel oil, etc.).

As mentioned above, the C18 or more LAO, which may be selectively used together with the C18 or more LAO derived from the MI range LAO, may be contained in an amount of, for example, about 50 wt % or less, particularly about 30 wt % or less, and more particularly about 20 wt % or less, based on the feed.

Double Bond Shift Reaction of Olefin

According to an embodiment of the present invention, a C18 or more LAO is converted into the corresponding LIO in the presence of a metal oxide catalyst, especially a catalyst having a weak acid site. Taking into consideration the properties of the catalyst, reaction conditions are controlled, so that the extent of double bond shift of the olefin may be adjusted. In an exemplary embodiment, the double bond shift reaction may be carried out even without the supply of hydrogen that is typically necessary for skeletal isomerization.

Although the present invention is not confined to specific theories, the reason why the olefin position in the C18 or more LAO is shifted is that the double bond in the olefin is shifted to the beta position while forming an unstable and weak bond with a metal oxide, and the olefin shifted to the beta position forms an unstable and weak bond with the adjacent metal oxide, all of which are repeated, thereby shifting the position of the double bond. As such, the double bond cannot be shifted to adjacent carbon, but may be shifted to only the beta position, and also the shift toward a longer carbon chain becomes prominent. Thus, as the double bond shift reaction progresses for a long period of time or becomes fast, the position of the double bond in the olefin converges toward the center thereof.

When the double bond shift rate in the olefin and the reaction time are increased in this way, the center LIO having a double bond positioned at the center thereof may result. At least some of double bonds or many double bonds in LIOs may be controlled to be present at the center of the carbon chain or at the position adjacent thereto, so that the pour point of the subsequent oligomerization product may be lowered, thereby manufacturing lube base oil having improved low-temperature properties.

In an exemplary embodiment, for the double bond shift reaction, the amount of the C18 or more center LIO based on the total C18 or more LIO may be, for example, at least about 25 wt %, particularly at least about 70 wt %, and more particularly at least about 90 wt %.

As the metal oxide catalyst for the double bond shift reaction, a wide variety of catalyst components may be used so long as they have weak acid sites. As such, the properties of the catalyst may be determined depending on the chain length distribution of the C18 or more LAO feed, and on whether isomers are contained therein. Taking into consideration the molecular size of the C18 or more LAO feed, a mesoporous or macroporous catalyst may be adopted. Examples of the catalyst having a weak acid site may include alumina, silica-alumina, zirconia, titania, iron oxide, vanadium oxide, zeolite (e.g. Y zeolite, A zeolite, ZSM-5, ZSM-48), and alumina-supported mesoporous silica. Particularly useful is alumina, zirconia, or titania, and alumina may be more particularly used.

In an exemplary embodiment, useful is an alumina catalyst having a BET specific surface area of at least about 150 m$^2$/g (particularly about 180~350 m$^2$/g, and more particularly about 200~300 m$^2$/g), an average pore size of at least about 5 nm (particularly about 6~20 nm, and more particularly about 7~15 nm), and a total pore volume of about 0.3~2.5 cc/g (particularly about 0.4~2.0 cc/g, and more particularly about 0.5~1.3 cc/g).

In a specific embodiment, the double bond shift reaction may be carried out at a temperature ranging from about 250° C. to less than about 400° C., particularly about 270~390° C., and more particularly about 300~375° C. As such, a metal oxide having a relatively weak acid site, such as zirconia, is reacted in the comparatively high temperature range among the above temperature ranges, whereas zeolite having a relatively strong acid site (especially Y zeolite) may be reacted in the comparatively low temperature range, and thereby the double bond shift reaction may be controlled.

As such, the reason why the reaction temperature is appropriately adjusted is that not only the double bond shift reaction but also side reactions such as cracking may occur together at a reaction temperature of predetermined level or more, thus incurring weight loss (weight reduction). In an exemplary reaction, as the reaction temperature is increased to about 200° C. or more, the double bond shift reaction takes place gradually, and then isomerization may occur together at about 350° C. or more. Also, isomerization may actively occur in the temperature range of about 400° C. or more, and simultaneously cracking may be additionally generated, undesirably causing the loss of the C18 or more LAO. The cracking reaction is a beta-scission reaction by the catalyst, ultimately producing ethylene. Hence, the C18 or more LAO may be converted to the corresponding LIO under the condition that the weight reduction may be suppressed as much as possible. As such, the weight reduction may be, for example, about 5 wt % or less, particularly about 3 wt % or less, and more particularly about 2 wt % or less.

Also, the reaction pressure may be adjusted in the range of, for example, about 4~40 bar, particularly about 5~20 bar, and more particularly about 6~10 bar. Although the present embodiment is not necessarily limited to the above pressure range, reaction activity may deteriorate under excessively high pressure conditions, whereas the feed may be lost at excessively low pressure. Hence, the pressure range may be appropriately adjusted.

In an exemplary embodiment, the catalyst may be applied in the form of a fixed bed (i.e. a fixed bed reactor), and thus may operate in a continuous mode. When a fixed bed reactor is used in this way, the reaction may be implemented with the supply of an inactive carrier gas. Examples of the inactive carrier gas may include nitrogen, argon, helium, and mixtures thereof, which may be selectively used without particular imitation so long as they are known in the art. More typically useful is nitrogen gas. As such, the flow rate of the inactive carrier gas into the fixed bed reactor may be considered as a factor able to control the reaction activity. Particularly, since the reaction is carried out by the contact between the catalyst and the feed, a retention time may be taken into account to control the reaction.

In this regard, when the flow rate of the inactive carrier gas is higher, the retention time between the catalyst and the feed may become short, and thus the double bond shift reaction occurs in a relatively small amount, and a probability of causing side reactions such as skeletal isomerization, cracking, etc. may comparatively decrease. In contrast, when the flow rate of the inactive carrier gas is lower, the double bond shift reaction occurs in a relatively large amount, and the amount of byproducts due to side reactions may also comparatively increase. In particular, when the temperature for the double bond shift reaction is high, side reactions may easily occur, and hence, the flow rate of the carrier gas is properly adjusted. In an exemplary embodiment, the flow rate of the inactive carrier gas into the reactor may be, for example, about 10~1000 sccm, particularly about 30~200 sccm, and more particularly about 50~100 sccm.

Also, a weight hourly space velocity (WHSV) upon fixed bed reaction may be adjusted in the range of, for example, about 0.01~50 hr$^{-1}$, particularly about 0.1~3 hr$^{-1}$, and more particularly about 0.5~1.5 hr$^{-1}$.

In an exemplary embodiment, the reaction product is separated after the double bond shift reaction, and a predetermined amount thereof (e.g. about 70 wt % or less, particularly about 1~50 wt %, and more particularly about 10~40 wt %) may be recycled to the reactor, and thus may be selectively converted to a center LIO (or LIO where a double bond is positioned close to the center).

Oligomerization of C18 or More LIO

In an embodiment of the present invention, the product obtained by the double bond shift reaction, namely, a C18 or more LIO may be converted into a hydrocarbon in the lube base oil range having an increased number of carbon atoms via oligomerization.

As such, the oligomerization product mainly includes a dimer and a trimer, and further includes a small amount (e.g. about 5 wt % or less, particularly about 3 wt % or less, and more particularly about 1 wt % or less) of tetramer or more oligomer. Typically, a dimer may be present as a main component.

The hydrocarbon produced by oligomerization may be adjusted so as to be imparted with the following properties:

Amount of dimer (D): at least about 30 wt % (particularly about 50~90 wt %, and more particularly about 60~80 wt %), Amount of trimer or more (T+): about 70 wt % or less (particularly about 10~50 wt %, and more particularly about 20~40 wt %), Ratio of dimer/trimer or more (D/T+ ratio; by weight): for example, at least about 0.1 (particularly 0.1~100, more particularly about 1~99, and much more particularly about 10~90), and Chain length (Number of carbon atoms of the longest carbon chain in an oligomer molecular structure): about 18~60 (particularly about 25~55, and more particularly about 36~50).

The α/β ratio of the oligomerization product is regarded as important. As mentioned above, the α/β ratio is affected by the properties of LIO resulting from the double bond shift reaction that is the previous step. Thus, the α/β ratio may act as a kind of benchmark for controlling the conditions of the double bond shift reaction.

In an embodiment, the α/β ratio may fall in the range of for example, about 1~10, particularly about 1~8, and more particularly about 1~6. As mentioned above, as the α/β ratio is lower, the viscosity index and the pour point may decrease. The produced hydrocarbon, which already has high viscosity index, may satisfy the requirements of Group III or Group III+ so long as the pour point may be lowered even when such a high viscosity index is slightly sacrificed.

In an exemplary embodiment, the oligomerization may be conducted using a batch reactor.

In an embodiment, the catalyst for use in oligomerization may be exemplified by a cationic polymerization catalyst, a metallocene catalyst, and a Ziegler-Natta catalyst. Typically useful is a cationic polymerization catalyst. As such, the catalyst may have non-sensitive characteristics for oxygen or air.

In an exemplary embodiment, examples of the cationic polymerization catalyst may include zeolite, or clay (especially, montmorillonite, kaolin, etc). Furthermore, a cationic polymerization catalyst such as SAPO or AlPO may be used, or alternatively useful is a catalyst configured such that aluminum (Al) is supported on mesoporous silica, such as SBA-15, MCM-41, or MCM-48 (where the amount of Al may be about 0.1~50 wt %, and particularly about 5~35 wt %). In this regard, zeolite is exemplified by Y-zeolite (especially USY zeolite having high SAR (Silica Alumina Ratio)), ZSM-5, and beta-zeolite. Also useful as Y-zeolite is USY zeolite having SAR of at least about 0.5, particularly at least about 12, more particularly about 30~150, and much more particularly about 50~100.

In addition thereto, hydrotalcite, a spinel type metal catalyst, or a strong acid site catalyst such as niobic acid may be used. Furthermore, a Y-zeolite/kaolin mixed RFCC catalyst (e.g. Y zeolite and kaoline are mixed at a ratio of 5~50 wt %), particularly a RFCC fresh catalyst or a RFCC Equilibrium catalyst (E-cat.), may be utilized.

In an exemplary embodiment, when a cationic polymerization catalyst is applied for oligomerization, the reaction may be carried out at a temperature of about 120~400° C. (particularly about 150~300° C., and more particularly about 180~250° C.). As such, the reaction may be implemented for about 1 min to 24 hr, and particularly about 30 min to 5 hr (batch reaction). Alternatively, the oligomerization may be performed in a continuous mode (e.g. using a CSTR reactor). In this case, WHSV may be, for example, about 0.01~10 hr$^{-1}$, and particularly about 0.1~5 hr$^{-1}$. After the oligomerization, cokes formed on the catalyst may be simply removed by air burning or firing, so that catalytic activity may become close to an initial state. Also, the oligomerization may be carried out in an oxygen-containing atmosphere, for example, in the presence of air.

When a metallocene or Ziegler-Natta catalyst is used, the reaction may be favorably carried out in a batch reactor at a temperature of about 100° C. or less, but the present invention is not necessarily limited thereto.

Selective Hydrogenation (Hydrotreating or Hydrofinishing)

In an embodiment, the hydrocarbon of the oligomerization product may contain a double bond in the molecular structure thereof. Thus, removal of the double bond (i.e. olefin) is required in consideration of oxidation stability of final products, and the double bond may be selectively removed by being saturated via hydrogenation known in the art.

In the hydrogenation, a catalyst for use in hydrogenation among typical refinery processes may be used without particular limitation. Particularly, the metal for hydrogenation may include any metal selected from among groups 8, 9, 10, 11, and 12 on the periodic table, and more particularly Pt, Pd, Ni, Fe, Cu, Cr, V, and Co, which may be used alone or in combination. More particularly, Pt and/or Pd may be used. Also, an inorganic oxide support, particularly at least one support of alumina, silica, silica-alumina, zirconia, ceria, titania, zeolite (e.g. Y zeolite (particularly having SAR of about 12 or more)), clay, SAPO, and AlPO may be provided in the form of being impregnated with the above metal component. As such, the metal may be used in an amount of, for example, about 0.1~30 wt %, particularly about 1~20 wt %, and more particularly about 3~15 wt %.

The hydrogenation conditions may include, for example, a reaction temperature of about 150~500° C. (particularly, about 180~350° C., and more particularly about 200~350° C.), a pressure of about 5~200 bar (particularly about 20~1.80 bar), and GOR (H$_2$/feed ratio) of about 300~2000 Nm$^3$/m$^3$ (particularly about 500~1500 Nm$^3$/m$^3$). Furthermore, in a continuous mode (for example using a CSTR reactor), the space velocity (WHSV) may be set to about 0.1~5 hr$^{-1}$, particularly about 0.1~3 hr$^{-1}$, and more particularly about 0.1~1 hr$^1$.

Selective Isomerization

As mentioned above, the typically produced material is an X-shaped hydrocarbon in the aforementioned embodiment, thus increasing low-temperature stability. Thus, upon manufacturing Group III or Group III+ lube base oil, there is no need to perform an isomerization process. However, when special lube base oil having superior low-temperature properties depending on the end-uses is manufactured, an isomerization process may be selectively added. For example, the use of a C18 or more LAO having a long hydrocarbon chain of the full range LAO may result in lube base oil having high viscosity and high viscosity index. As such, when special lube oil is produced, an isomerization process may be additionally performed, as necessary.

Such an isomerization process may be performed in the presence of a catalyst configured such that group 10 metal (e.g. a precious metal such as Pt or Pd) alone or in combination is supported on mesoporous zeolite (e.g. EU-1, ZSM-35, ZSM-11, ZSM-57, NU-87, ZSM-22, EU-2, EU-11, ZBM-30, ZSM-48, ZSM-23 or mixtures thereof). As such, the metal component may be used in an amount of, for example, about 0.1~3 wt %, particularly about 0.3~1.5 wt %, and more particularly about 0.3~1 wt %.

The lube base oil thus manufactured may have a viscosity index of at least 130, a pour point of −20° C. or less, and a cloud point of −20° C. or less, and may satisfy requirements of Group III or Group III+.

A better understanding of the present invention may be obtained via the following examples which are set forth to illustrate, but are not to be construed as limiting the present invention.

EXAMPLES

Figure 2:
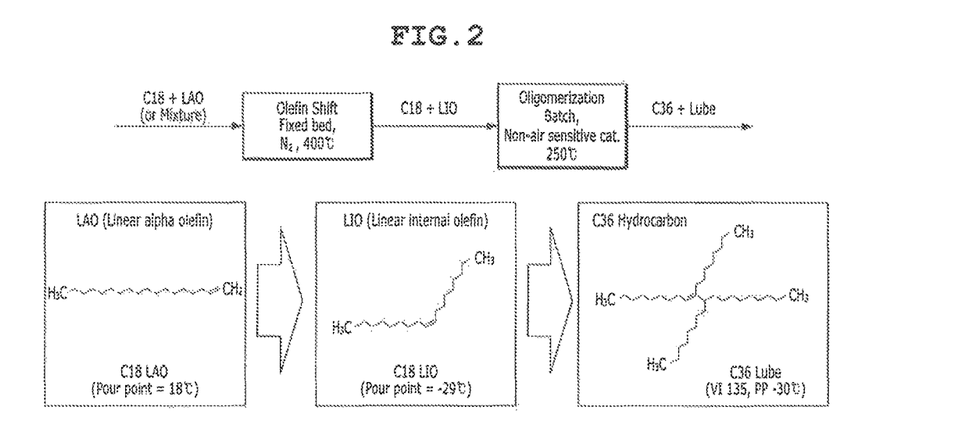
FIG. 2 schematically illustrates the procedure of production of lube base oil from a C18 LAO (1-octadecene) in Examples 1 and 2.

Lube base oil was manufactured from a C18 LAO through the process as illustrated in FIG. 2.

Example 1

Olefin Shift Reaction in N$_7$ Atmosphere

As a C18 LAO, 1-octadecene was subjected to olefin shift in a fixed bed reactor. Specifically, 6 g of an alumina catalyst (SA6275 made by Saint Gobain Norpro) was fed into the fixed bed reactor, and the top and the bottom of the catalyst were covered with glass wool, and the remaining portion of the reactor was filled with silica beads, after which a thermocouple was mounted so as to be in contact with the portion of the reactor filled with the catalyst. As such, alumina having a. BET specific surface area of 260 m$^2$/g, an average pore size of 10 nm, and a total pore volume of 0.83 cc/g was used.

Under conditions of N$_2$ at 5 bar and 100 sccm, the reactor was heated at a rate of 5° C./min, and maintained at 400° C. for 3 hr, so that water or adsorptive gas present on the surface of the catalyst was removed. Subsequently, the temperature was lowered to 250° C., and the C18 LAO was fed at 0.13 sccm, and the reactor was operated at WHSV of 1 hr$^{-1}$.

Draining was performed up to initial 16 hr, after which sampling was conducted at intervals of 8 hr, and LIO conversion activity and selectivity were measured. The reaction activity was checked at 250° C., and then measured up to 400° C. while the reaction temperature was additionally increased. After changes in the conditions, the results showing a stable product pattern after two days, taking into consideration the reaction stability, were adopted.

The conversion rate of the produced LIO was checked through Simdist. The produced gas was measured by GC, and the selectivity of the product and the side reactions were checked through GC-MS and Simdist.

Figure 3:
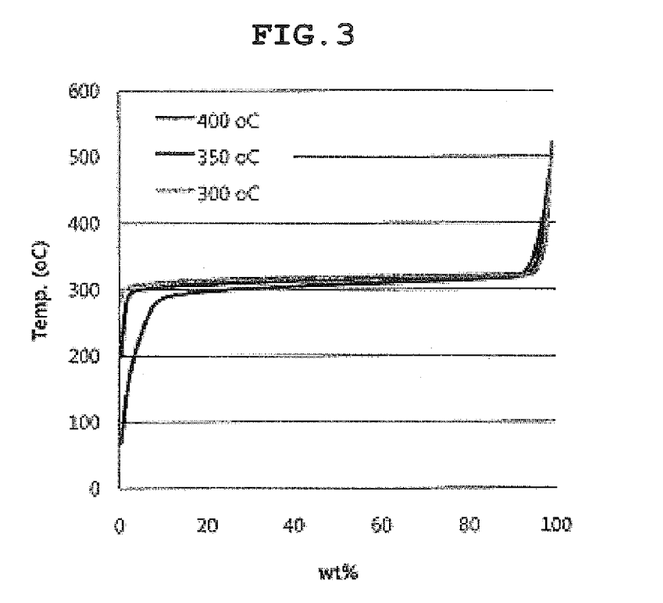
FIG. 3 is a graph illustrating the results of Simdist analysis of the product obtained by olefin shift of the C18 LAO (1-octadecene) in Example 1.

Depending on changes in the reaction temperature from 250° C. to 400° C., the results of Simdist analysis of the product obtained by the double bond shift reaction of the C18 LAO are shown in FIG. 3.

As illustrated in FIG. 3, there was no substantial difference in the pattern of the product relative to the C18 LAO at a reaction temperature of 300° C. However, weight reductions of 2 wt % and 9 wt % were measured at 350° C. and 400° C., respectively.

Figure 4:
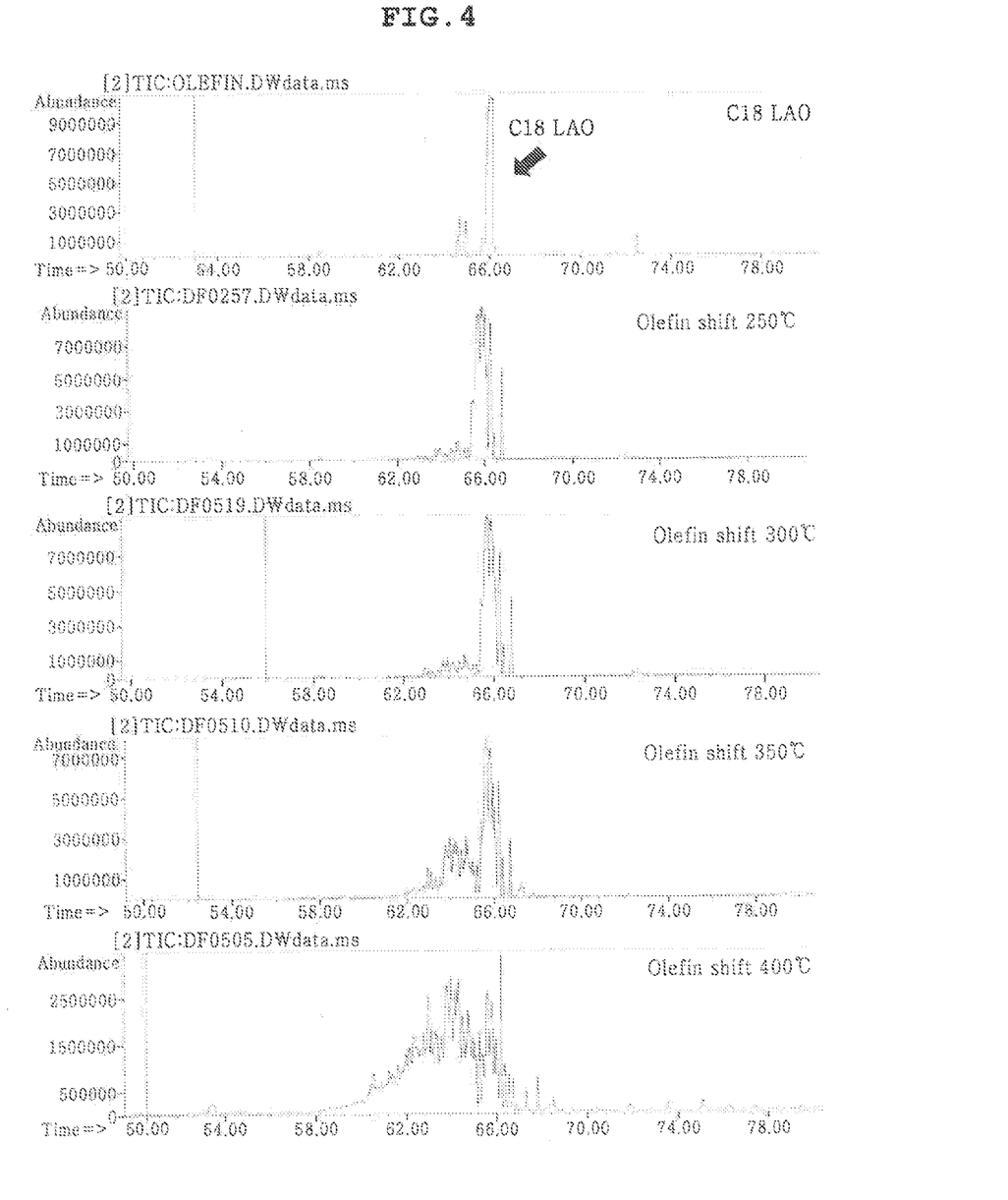
FIG. 4 is a graph illustrating the results of GC-MS analysis of the product obtained by olefin shift of the C18 LAO (1-octadecene) depending on the reaction temperature (250° C., 300° C., 350° C., and 400° C.) in Example 1.

Also, the results of GC-MS analysis of the product at a reaction temperature from 250° C. to 400° C. are shown in FIG. 4.

As illustrated in FIG. 4, the product obtained by double bond shift reaction at 300° C. or less was not significantly changed in the product pattern based on the results of Simdist analysis, but the LAO position shifted to the LIO based on the results of GC-MS analysis. However, at a reaction temperature of 350° C., the amount of branched LIO resulting from skeletal isomerization was gradually increased. At a reaction temperature of 400° C., not only the branched LIO resulting from skeletal isomerization but also C16 and C17 LIOs resulting from cracking were produced.

Based on the above measurement results, upon conversion from the C18 LAO into the C18 LIO, only the double bond shift reaction in the molecular structure occurred at 300° C. or less, and skeletal isomerization also took place in the reaction temperature range up to 350° C., thus producing a C18 branched LIO, from which the weight reduction of 2 wt % was caused. Then, in the reaction temperature range up to 400° C., both skeletal isomerization and cracking were generated, undesirably incurring the weight reduction.

The pour point and the cloud point of the C18 LAO-derived LIOs were measured. The results are given in Table 3 below, together with the amount of center LIO of the product and the weight reduction.

TABLE 3

| Olefin | Reaction Temp. (° C.) | Pour point (° C.) | Cloud point (° C.) | Weight reduction (%) | Amount of center LIO of product (wt %) |
|---|---|---|---|---|---|
| C18 LAO | — | 18 | 20 | — | 0 |
|  | 250 | −6 | −5 | 0 | 28 |
|  | 300 | −10 | −8 | 0 | 73 |
|  | 350 | −15 | −13 | 2 | 97 |
|  | 375 | −18 | −17 | 3 | 100 |
|  | 400 | −29 | −25 | 9 | 100 |

As is apparent from Table 3, the pour point and the cloud point of the C18 LAO were as high as 18° C. and 20° C., respectively, but could be simply remarkably lowered through the double bond shift reaction at a reaction temperature of 250° C. Also, the pour point and the cloud point were gradually decreased with an increase in the reaction temperature. At a reaction temperature of 350° C. at which skeletal isomerization is initiated, the pour point and the cloud point of the product were −15° C. and −13° C., respectively, and at a reaction temperature of 400° C. at which skeletal isomerization and cracking take place more actively, the pour point and the cloud point of the product were drastically lowered to −29° C. and −25° C., respectively.

Example 2

Oligomerization of C18 LIO

In a 500 cc glass flask, 200 g of the C18 LIO obtained from the C18 LAO at different double bond shift reaction temperatures (250° C., 300° C., 350° C., 375° C., and 400° C.) was placed as in Example 1, and 20 g of zeolite as an oligomerization catalyst was further added. As such, the zeolite catalyst was Y-zeolite having SAR of 80. Then, the reaction mixture was heated to 180° C. with stirring at 500 rpm. When the reaction temperature reached 180° C., the reaction was maintained for about 3 hr and then stopped.

After termination of the reaction, the mixture of the catalyst and the reaction product was filtered, so that the catalyst and the reaction product were separated from each other. The separated catalyst was stored for regeneration, and the reaction product was stored for subsequent hydrogenation.

The hydrogenation was carried out using a NiMo/ZrO$_2$ catalyst in a CSTR reactor, under the reaction conditions of 200° C., H$_2$ pressure of 20 bar, WHSV of 0.5 hr$^{-1}$, and GOR of 1000 Nm$^3$/m$^3$, thereby selectively removing the double bond from the reaction product.

The oligomerization product was subjected to Simdist analysis to check the reaction yield, and also the generation of side reactions was checked through GC-MS analysis.

Figure 5:
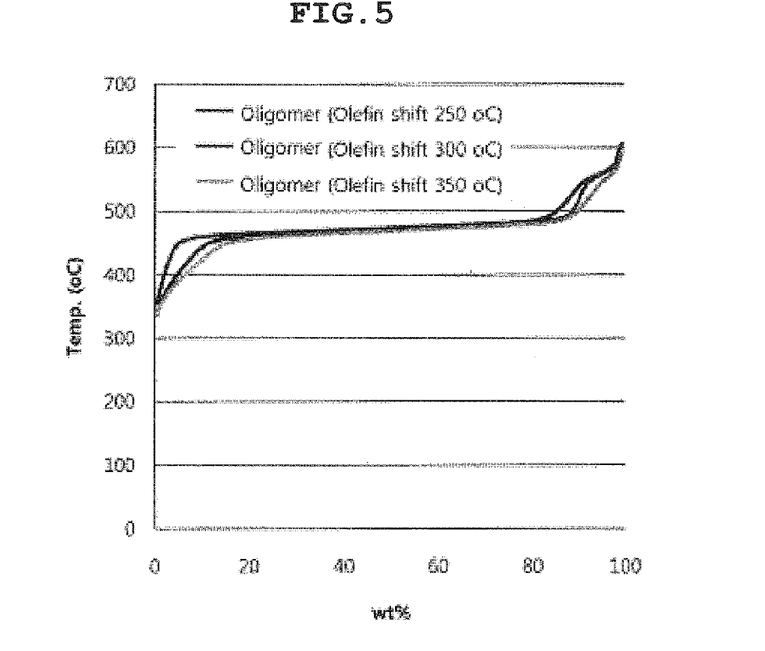
FIG. 5 is a graph illustrating the results of Simdist analysis of the product (reaction temperature for olefin shift of C18 LAO: 250° C., 300° C., and 350° C.) obtained by oligomerization of the C18 LIO in Example 2.

In this regard, the results of Simdist analysis of the product obtained by oligomerization of the C18 LIO (olefin shift reaction temperature of C18 LAO: 250° C., 300° C., and 350° C.) are shown in FIG. 5.

As illustrated in FIG. 5, the oligomerization product was composed mainly of a C36 dimer having a boiling point of 450~490° C., with a small amount of trimer at about 550° C. As the double bond shift reaction temperature was higher, the slope of the dimer pattern in the oligomer by Simdist became gentle, which is evaluated to be due to not the single material but the monomers in isomer form provided in a larger amount. Since the reaction product is an oligomer of two monomers, it is considered to be significantly affected.

Figure 6:
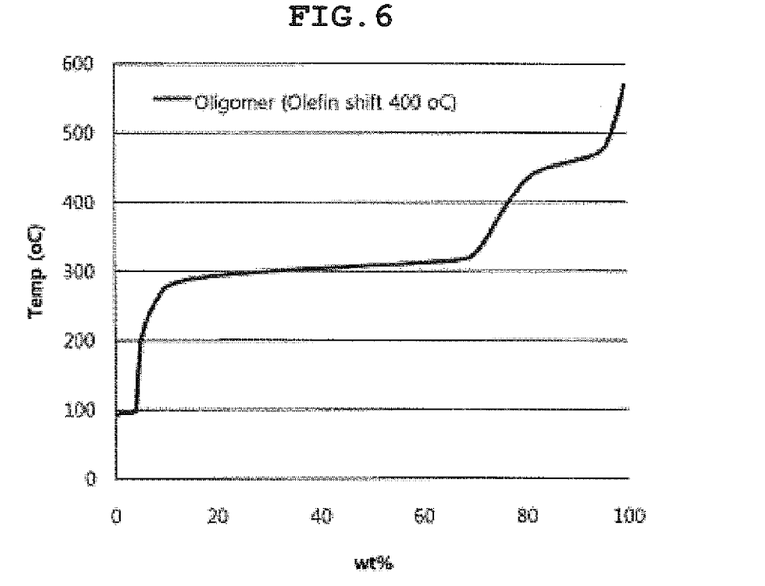
FIG. 6 is a graph illustrating the results of Simdist analysis of the product (reaction temperature for olefin shift of C18 LAO: 400° C.) obtained by oligomerization of the C18 LIO in Example 2.

Also, the results of Simdist analysis of the product obtained by oligomerization of the C18 LIO (olefin shift reaction temperature of C18 LAO: 400° C.) are illustrated in FIG. 6.

The lube base oil was typically a hydrocarbon having a boiling point of 340° C. or more, and the slope of the dimer pattern at 340° C. or more was very gentle. This is considered to be due to a variety of constituents of the C18 LIO corresponding to the monomers. In particular, since skeletal isomerization and cracking simultaneously occur in the double bond shift reaction at 400° C., the monomer composition participating in the oligomerization may become very various.

To evaluate the properties of the lube base oil, viscosity at each of 40° C. and 100° C. was measured, from which the viscosity index was calculated. Also, the pour point of the obtained C18 LIO oligomer was measured, and applicability thereof to lube base oil was checked. In addition thereto, the average α/β value and the dimer (D)/trimer or more (T+) weight ratio were determined.

The measurement results depending on the double bond shift reaction temperature of the C18 LAO are shown in Table 4 below.

TABLE 4

| Double bond shift temp. of C18 LAO (° C.) | Oligomerization yield (%) | Average α/β | D/T + weight ratio | Viscosity (cps) 40° C. | Viscosity (cps) 100° C. | Viscosity index (a.u.) | Pour point (° C.) |
| --- | --- | --- | --- | --- | --- | --- | --- |
| — | 85 | 5.1 | 8.1 | 25.68 | 5.77 | 178 | −7 |
| 250 | 71 | 3.7 | 6.7 | 25.25 | 5.34 | 152 | −15 |
| 300 | 68 | 1.7 | 6.7 | 26.49 | 5.42 | 145 | −21 |
| 350 | 57 | 1.4 | 5.7 | 25.79 | 5.23 | 138 | −21 |
| 375 | 51 | 1.2 | 5.7 | 27.59 | 5.42 | 135 | −30 |
| 400 | 32 | 1.1 | 4.9 | 31.01 | 5.52 | 115 | <−53 |

As is apparent from Table 4, when the LIO obtained by converting the C18 LAO at a relatively high temperature is used as an oligomerization feed, the oligomerization yield is decreased. This is considered to be because the oligomerization activity deteriorates due to steric hindrance as the double bond in the olefin is positioned at the center. In terms of properties, the product satisfying the requirements of Group III or Group III+ lube base oil is an oligomer of the C18 LIO prepared at a double bond shift reaction temperature of 300~375. As such, the production yield of the lube base oil approximates to 51~68%, but may be supplemented through recycling.

The oligomerization product of the C18 LIO obtained at a double bond shift reaction temperature of 400° C. had a pour point of −53° C. or less and thus exhibited superior low-temperature properties, but possessed a relatively low viscosity index of 115, and thus did not satisfy the requirements of Group III or Group III+ corresponding to the high-quality lube base oil. This may be explained because branched olefins of less than C18 produced by skeletal isomerization and cracking participated in the oligomerization reaction.

The product obtained by the oligomerization of the C18 LIO is an olefin having one double bond, and the double bond thereof may be removed because it may deteriorate stability in order to achieve industrial applicability. To evaluate the effects of hydrogenation, the viscosity (40° C. and 100° C.), viscosity index, pour point and cloud point after hydrogenation of the oligomerization product (oligomerization product of the C18 LIO produced at a double bond shift reaction temperature of 375° C.) were measured. The measurement results are shown together with the properties before hydrogenation in Table 5 below.

TABLE 5

| | Viscosity (cps) 40° C. | Viscosity (cps) 100° C. | Viscosity index (a.u.) | Pour point (° C.) | Cloud point (° C.) |
| --- | --- | --- | --- | --- | --- |
| Before hydrogenation | 27.59 | 5.42 | 135 | −30 | −30 |
| After hydrogenation | 30.23 | 5.70 | 132 | −30 | −29 |

As is apparent from Table 5, the oligomer (lube base oil) resulting from hydrogenation of the olefin was slightly decreased in viscosity index, but was not significantly changed in the overall properties. Rather, the viscosity at 100° C., which is regarded as important, was increased from 5.42 to 5.70, thus exhibiting superior properties.

Accordingly, simple modifications or variations of the present invention may be easily utilized by those having ordinary knowledge in the art, and should also be understood as falling within the scope of the present invention.

What is claimed is:

1. A method of manufacturing lube base oil from linear alpha-olefin, comprising:
   a) providing one or more linear alpha-olefin(s) having 18 or more carbons;
   b) converting the linear alpha-olefin(s) into linear internal-olefin(s) having 18 or more carbons by a double bond shift reaction at a temperature ranging from 250° C. to less than 400° C. in the presence of a catalyst having weak acid sites; and
   c) oligomerizing the linear internal-olefin(s), thus synthesizing a lube base oil having an X-shaped hydrocarbon;
   wherein
   in b), a weight reduction of the linear internal-olefin(s) relative to the linear alpha-olefin(s) is 5% or less;
   in c), the X-shaped hydrocarbon in the lube base oil range has a α/β value of 1-10 (where α is a number of carbon atoms of a longest carbon chain in the X-shaped hydrocarbon, and β is a number of carbon atoms of a shortest carbon chain in the X-shaped hydrocarbon), and includes a dimer (D) and a trimer or higher oligomers (T+) X-shaped hydrocarbon of the linear internal-olefin(s), with a D/T+ weight ratio ranging from 0.1 to 100;
   wherein the catalyst having weak acid sites is a mesoporous catalyst or a macroporous catalyst and the double bond shift reaction is conducted in mesopores of the mesoporous catalyst or macropores of the macroporous catalyst, and
   wherein the catalyst having a weak acid site is one or more catalyst selected from the group consisting of alumina, silica-alumina, zirconia, titania, iron oxide, vanadium oxide, zeolite, and alumina-supported mesoporous silica.

2. The method of claim 1, wherein the one or more linear alpha-olefin(s) having 18 or more carbons is one or more linear alpha-olefin(s) having 18 or more carbons having an even number of carbon atoms, derived from a C4-C40 full range linear alpha-olefin produced by ethylene polymerization or oligomerization.

3. The method of claim 2, wherein the one or more linear alpha-olefin(s) having 18 or more carbons further comprises one or more linear alpha-olefin(s) having 18 or more carbons derived from Fischer-Tropsch reaction.

4. The method of claim 1, wherein the number of carbon atoms of the longest carbon chain in a molecular structure of the X-shaped hydrocarbon in the lube base oil range is 20-60.

5. The method of claim 1, wherein b) is performed at a temperature of 300-375° C.

6. The method of claim 1, wherein b) is performed at a pressure of 4-10 bar.

7. The method of claim 1, wherein b) is performed in a fixed bed reactor.

8. The method of claim 7, wherein b) is performed at a weight hourly space velocity (WHSV) of 0.01-50 hr$^{-1}$ and at an inactive carrier gas flow rate of 10-1000 sccm.

9. The method of claim 8, wherein the inactive carrier gas is nitrogen, argon, helium, or a mixture thereof.

10. The method of claim 1, wherein the alumina has a BET specific surface area of at least 150 m$^2$/g, an average pore size of at least 5 nm, and a total pore volume of 0.5-1.3 cc/g.

11. The method of claim 1, wherein the linear internal-olefin(s) having 18 or more carbons produced in b) contains at least 25 wt % of a one or more center linear internal-olefin(s) having 18 or more carbons.

12. The method of claim 1, wherein the one or more linear alpha-olefin(s) having 18 or more carbons is one or more linear alpha-olefin(s) having 20 or more carbons.

13. The method of claim 1, wherein c) is performed in the presence of a cationic polymerization catalyst, wherein the cationic polymerization catalyst comprises zeolite, clay, SAPO, AlPO, or a catalyst configured such that aluminum (Al) is supported on mesoporous silica.

14. The method of claim 13, wherein the clay is montmorillonite, and wherein the zeolite is a Y-zeolite having a silica alumina ratio of 30-150, an RFCC catalyst, or beta-zeolite.

15. The method of claim 1, wherein c) is performed at a temperature of 120-400° C.

16. The method of claim 1, wherein c) is performed in an oxygen-containing atmosphere using a batch reactor.

17. The method of claim 1, wherein c) is performed using a continuous reactor at a weight hourly space velocity (WHSV) of 0.01-10 hr$^{-1}$.

18. The method of claim 1, further comprising performing hydrogenation to remove a double bond from the lube base oil, after c).

19. The method of claim 1, further comprising performing isomerization of the linear internal-olefins(s) and/or the lube base oil to additionally improve low-temperature properties, before and/or after c).

20. The method of claim 19, wherein the lube base oil in c) is lube base oil satisfying requirements of Group III+.

* * * * *

UNITED STATES PATENT AND TRADEMARK OFFICE
CERTIFICATE OF CORRECTION

PATENT NO. : 10,322,980 B2
APPLICATION NO. : 14/693326
DATED : June 18, 2019
INVENTOR(S) : Hee Jung Jeon et al.

It is certified that error appears in the above-identified patent and that said Letters Patent is hereby corrected as shown below:

On the Title Page

Under (71) Applicant:
Please replace the second applicant name from "SK LUBRICANTS CO., LTD., Seoul (KR)" to "SK ENMOVE CO., LTD., Seoul (KR)"; and Under (73) Assignee:
Please replace the second assignee name from "SK LUBRICANTS CO., LTD., Seoul (KR)" to "SK ENMOVE CO., LTD., Seoul (KR)".

Signed and Sealed this
Thirteenth Day of August, 2024

Katherine Kelly Vidal
*Director of the United States Patent and Trademark Office*